United States Patent [19]

Block et al.

[11] 4,307,040
[45] Dec. 22, 1981

[54] PROCESS FOR PRODUCING PHOSPHONOMALEIC ACID ESTERS

[75] Inventors: Hans-Dieter Block, Cologne; Friedrich Schwochow, Leverkusen; Reinhard Schliebs, Cologne, all of Fed. Rep. of Germany

[73] Assignee: Bayer Aktiengesellschaft, Leverkusen, Fed. Rep. of Germany

[21] Appl. No.: 140,891

[22] Filed: Apr. 16, 1980

[30] Foreign Application Priority Data

May 5, 1979 [DE] Fed. Rep. of Germany ....... 2918161

[51] Int. Cl.$^3$ ............................................. C07F 9/40
[52] U.S. Cl. .................................................. 260/986
[58] Field of Search ............................... 260/942, 986

[56] References Cited

U.S. PATENT DOCUMENTS

| | | | |
|---|---|---|---|
| 2,888,434 | 5/1959 | Shashous | 260/986 |
| 2,959,609 | 11/1960 | Leupold et al. | 260/986 |
| 3,064,030 | 11/1962 | Chadwick et al. | 260/986 |
| 3,064,053 | 11/1962 | Rabinowitz | 260/986 |
| 3,562,166 | 2/1971 | Nicholson et al. | 260/942 |
| 3,579,570 | 5/1971 | Nicholson et al. | 260/502.4 P |
| 3,933,944 | 1/1976 | Moreau et al. | 260/932 |
| 4,113,861 | 9/1978 | Fleisch et al. | 424/204 |

OTHER PUBLICATIONS

Huff et al., "J. Chem. Soci., Perkin Trans.", I, 1972 (20), pp. 1584–1590.
Hagele, et al. "Phosphorus & Sulfur", 1977, vol. 3, pp. 47–50.

*Primary Examiner*—Anton H. Sutto
*Attorney, Agent, or Firm*—Sprung, Felfe, Horn, Lynch & Kramer

[57] ABSTRACT

Novel phosphonomaleic acid esters of the formula $$\begin{array}{c} R^1-(O)_n \quad O \quad\quad O \\ \diagdown \| \quad\quad \| \\ P-C-C-OR^3 \\ \diagup \quad\quad \| \\ R^2-O \quad\quad C-C-OR^4 \\ \diagup \quad \| \\ R^5 \quad O \end{array}$$

in which
  $R^1$ is an optionally substituted alkyl radical containing from 1 to 6 carbon atoms and, where n=0, may also be an optionally substituted aryl radical,
  $R^2$, $R^3$ and $R^4$ each independently is an optionally substituted alkyl radical containing from 1 to 16 carbon atoms,
  $R^5$ is hydrogen, an alkyl or aryl radical containing from 1 to 7 carbon atoms, and
  n=0 or 1, are produced by reacting a base with a 1-halogen-1-phosphonosuccinic acid ester of the formula $$\begin{array}{c} R^1-(O)_n \quad O \quad Hal \quad O \\ \diagdown \| \quad | \quad\quad \| \\ P-C----C-O-R^3 \\ \diagup \quad\quad | \\ R^2-O \quad\quad CH-C-O-R^4 \\ \diagup \quad \| \\ R^5 \quad O \end{array}$$

in which Hal is chlorine or bromine.

The esters are useful as intermediates in the synthesis of sequestrants, corrosion inhibitors, stabilizers, flame-proofing agents, pharmaceuticals and pesticides.

4 Claims, No Drawings

PROCESS FOR PRODUCING PHOSPHONOMALEIC ACID ESTERS

This invention relates to phosphonomaleic acid esters corresponding to the following general formula (I):

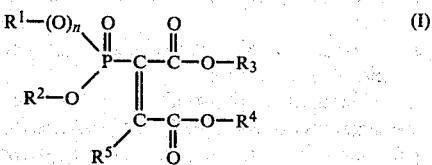

in which $R^1$ represents an optionally substituted alkyl radical containing from 1 to 16 carbon atoms and, where n=0, also represents an optionally substituted aryl radical, $R^2$, $R^3$ and $R^4$ independently of one another represent an optionally substituted alkyl radical containing from 1 to 16 carbon atoms, $R^5$ represents hydrogen or an alkyl or aryl radical containing from 1 to 7 carbon atoms, and n=0 or 1.

The present invention also relates to a process for producing the phosphonomaleic acid esters corresponding to the general formula (I) which is characterized in that 1-halogen-1-phosphonosuccinic acid esters corresponding to the following formula (II):

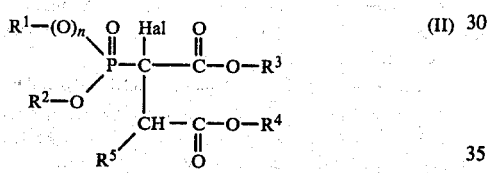

in which
Hal represents fluorine, chlorine or bromine,
$R^1$ represents an optionally substituted alkyl radical containing from 1 to 16 carbon atoms and, where n=0, also represents an optionally substituted aryl radical,
$R^2$, $R^3$ and $R^4$ independently of one another represent an alkyl radical containing from 1 to 16 carbon atoms,
$R^5$ preferably represents hydrogen or an alkyl or aryl radical, and
n=0 or 1,
are reacted with bases.

The phosphonomaleic acid esters are highly reactive monomers which lend themselves to a large number of reactions among which the addition reactions occupy a prominent position by virtue of the double bond present in the molecule. They are suitable for the synthesis of active substances such as, for example, sequestrants, corrosion inhibitors, stabilizers, flameproofing agents, pharmaceuticals and pesticides. Corresponding agents are described, for example, in U.S. Pat. No. 3,579,570, in U.S. Pat. No. 3,933,944 or in German Offenlegungsschrift No. 2,819,112.

Those compounds are preferred in which $R^1$, $R^2$, $R^3$ and $R^4$ each independently is alkyl or alkoxyalkyl containing from 1 to 12 and especially 1 to 4 carbon atoms per alkyl moiety, e.g. 1 or 2 carbon atoms per alkyl moiety and particularly 1 carbon atom, although $R^1$ may also be phenyl when n=0. $R^5$ is preferably hydrogen or methyl. Where optional substituents are present they are preferably halo, alkyl, hydroxy alkyl, or alkoxy of 1 to 4 carbon atoms per alkyl moiety.

The method according to the invention for producing phosphonomaleic acid esters is surprising insofar as, hitherto, it has only been possible to produce unsaturated phosphonic acid esters from 2-chloro- or 2-bromo-alkane phosphonic acid esters with bases and not from 1-bromo- or 1-chloro-alkane phosphonic acid esters of the type present in 1-halogen-1-phosphonosuccinic acid esters (hereinafter referred to in short as 1-halogen phosphonosuccinic acid esters). Even where 1,2-dibromo or 1,2-dichloro-alkane phosphonic acid esters are used, it is only the halogen atom in the β-position and never the α-halogen atom which is split off as hydrogen halide by reaction with bases.

Starting materials for producing the phosphonomaleic acid esters of the formula (I) in accordance with the invention are the 1-halogen phosphonosuccinic acid esters corresponding to the formula (II), which in turn may readily be prepared by halogenating phosphonosuccinic acid esters corresponding to the following formula (III):

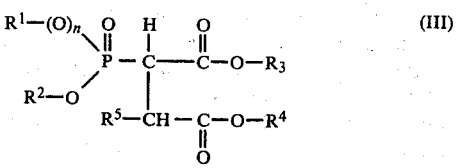

in which $R^1$, $R^2$, $R^3$, $R^4$, $R^5$ and n have the same meaning as in the formula (I). Halogenation may be carried out with hypohalites and also with the elemental halogens chlorine and bromine, with inter-halogen compounds, or with halogen-yielding compounds, for example cage compounds containing elemental halogen, in the presence of hydrogen halide acceptors, optionally in the presence of solvents and optionally in the presence of a buffer system.

Examples of phosphonosuccinic acid esters suitable for producing the 1-halogen phosphonosuccinic acid esters used in the process according to the invention are the following:
dimethoxy phosphonosuccinic acid dimethyl ester,
diethoxy phosphonosuccinic acid diethyl ester,
di-n-butyoxy phosphonosuccinic acid di-n-butyl ester,
di-i-butoxy phosphonosuccinic acid di-i-butyl ester,
di-sec-butoxy phosphonosuccinic acid di-sec-butyl ester,
di-2-ethylhexyl phosphonosuccinic acid di-2-ethylhexyl ester,
didodecyloxy phosphonosuccinic acid didodecyl ester,
diethoxy phosphonosuccinic acid dibutyl ester,
dimethoxy phosphonosuccinic acid di-2-butoxyethyl ester,
dimethoxy phosphonosuccinic acid dicyclohexyl ester,
dimethoxy phosphonosuccinic acid bis-triethylene glycol ester,
dimethoxy phosphonosuccinic acid bis-2-chloroethyl ester,
bis-2-ethoxyethoxy phosphonosuccinic acid dimethyl ester,
methyl methoxy phosphonosuccinic acid dimethyl ester,
methyl ethoxy phosphonosuccinic acid diethyl ester,
ethyl methoxy phosphonosuccinic acid dimethyl ester, phenyl methoxy phosphonosuccinic acid dimethyl ester,
2-methyl-1-(dimethyl phosphono)-succinic acid dimethyl ester,
and mixed esters thereof, of the type generally formed spontaneously and freely by transesterification from phosphonosuccinic acid esters containing different alkoxy radicals in the molecule.

In the naming of the phosphonosuccinic acid esters mentioned by way of example above and the 1-halogen phosphonosuccinic acid esters mentioned by way of example below, the alkoxy or alkyl radicals attached to the group P=0 (phosphono group) precede the phosphono group as a prefix, whereas the alcohols attached to the carboxyl groups as esters follow the name of the acid.

The phosphonosuccinic acid esters are compounds which may readily be obtained by known methods and some of which have already been produced on a commercial scale (cf. for example, Journal of General Chemistry of the USSR, 24, pages 121-124 (1954). They are produced by an addition reaction between dialkyl phosphites or akyl phosphonites and maleic or fumaric acid esters or even by the esterification of phosphonosuccinic acid partial esters of the type formed, for example, in the reaction of trialkyl phosphites or dialkyl phosphonites with fumaric acid or maleic acids, or even by the reaction of trialkyl phosphites or dialkyl phosphonites with maleic acid or fumaric acid monoalkyl esters.

Examples of 1-halogen phosphonosuccinic acid esters suitable for the process according to the invention are the following:
1-chloro-dimethoxy phosphonosuccinic acid dimethyl ester,
1-chloro-diethoxy phosphonosuccinic acid diethyl ester,
1-chloro-di-n-butoxy phosphonosuccinic acid di-n-butyl ester,
1-chloro-di-i-butoxy phosphonosuccinic acid di-i-butyl ester,
1-chloro-di-sec-butoxy phosphonosuccinic acid di-sec-butyl ester,
1-chloro-di-2-ethylhexyl phosphonosuccinic acid di-2-ethyl hexyl ester,
1-chloro-didodecyloxy phosphonosuccinic acid didodecyl ester,
1-chloro-diethoxy phosphonosuccinic acid dibutyl ester,
1-chloro-dimethoxy phosphonosuccinic acid di-2-butoxyethyl ester,
1-chloro-dimethoxy phosphonosuccinic acid dicyclohexyl ester,
1-chloro-dimethoxy phosphonosuccinic acid bis-triethylene glycol ester,
1-chloro-dimethoxy phosphonosuccinic acid bis-2-chloroethyl ester,
1-chloro-bis-2-ethoxyethoxy phosphonosuccinic acid dimethyl ester,
1-chloro-methyl methoxy phosphonosuccinic acid di-methyl ester,
1-chloro-methyl ethoxy phosphonosuccinic acid diethyl ester,
1-chloro-ethyl methoxy phosphonosuccinic acid dimethyl ester,
1-chloro-phenyl methoxy phosphonosuccinic acid dimethyl ester,
1-bromo-dimethoxy phosphonosuccinic acid dimethyl ester,
1-bromo-diethoxy phosphonosuccinic acid diethyl ester,
1-bromo-methyl methoxy phosphonosuccinic acid dimethyl ester,
1-fluoro-dimethoxy phosphonosuccinic acid dimethyl ester,
1-chloro-2-methyl-1-(dimethoxy phosphono)-succinic acid dimethyl ester,
and mixed esters thereof, of the type generally formed spontaneously and freely by transesterification from phosphonosuccinic acid esters containing different alkoxy radicals in the molecule.

Bases suitable for converting the halogen phosphonosuccinic acid esters into phosphonomaleic acid esters belong both to the group of basically acting nitrogen compounds and phosphorus compounds and also to the class of ionic compounds having a basically acting anion.

Suitable basic nitrogen compounds are, for example, amines, for example trialkyl amines, aryl amines, alkyl aryl amines and associated polyamines and saturated and unsaturated 5-membered, 6-membered and 7-membered nitrogen heterocycles as well as amides and nitriles. Suitable basic phosphorus compounds are, for example, trialkyl phosphines, hydrocyalkyl phosphines, trialkyl phosphites, alkyl aryl phosphites, alkyl phosphonites and alkyl phosphonites. Preferred alkyl moieties contain 1 to 4 carbon atoms and the preferred aryl moiety is phenyl.

Suitable ionic compounds with basically acting anions include, for example, hydroxides, oxides, amides, alcoholates, phenolates, carbonates, hydrogen carbonates, phosphates, hydrogen phosphates, monoalkyl phosphates, phosphites, polyphosphates, metaphosphates, phosphonates, silicates, hydroxy and oxo complexes of metals, such as zincates, aluminates or stannates, preferably in the form of their alkali metal, alkaline earth metal and ammonium salts and also the salts of carboxylic acids, for example fatty acids, polycarboxylic acids, aminocarboxylic acids, hydroxy carboxylic acids and phosphonocarboxylic acids. It is also possible to use mixtures of different bases. The effect of the bases may also be modified by the addition of buffering substances.

To obtain an optimum reaction result, the base used, the 1-halogen phosphonosuccinic acid ester to be reacted and the other reaction conditions have to be co-ordinated with one another in order in particular to prevent dealkylation of the 1-halogen phosphonosuccinic acid ester and the phosphonomaleic acid ester formed therefrom by the base and the base hydrohalide or by the halide formed from the base and the hydrogen halide eliminated.

The 1-halogen phosphonosuccinic acid ester and the base are preferably used in a molar ratio of about 1:1. If desired, it is even possible to use an excess of base, whereas a deficit of base results in an incomplete reaction. Larger deviations from the molar ratio of 1:1 generally afford no advantages.

It is, of course, also possible to carry out halogenation of the phosphonosuccinic acid ester of the formula (III) to form the 1-halogen phosphonosuccinic acid ester of the formula (II) and the conversion of the 1-halogen phosphonosuccinic acid ester of the formula (II) into the phosphonomaleic acid ester of the formula (I) in the form of a one-pot reaction, in which case the hydrogen halide acceptor used for the first reaction and the base required for the second reaction may be the same or different and the two reaction steps may be carried out either simultaneously or successively.

The process according to the invention may be carried out in the presence or absence of solvents. In this connection, both single-phase liquid systems and also two-phase liquid systems with or without a solid phase may occur. The solvent may even be identical with the base used. Suitable solvents are, for example, water, alcohols, ethers, hydrocarbons and chlorinated hydrocarbons, acid amides and nitriles. Where alcohols are used as solvent and particularly where alcoholates are used as the bases in alcohols as solvent, it is preferred to co-ordinate the alcohol and alcoholate used with the alcohols present in esterified form in the 1-halogen phosphonosuccinic acid ester to be reacted and to make them as alike as possible. Where the process is carried out in two-phase liquid systems, phase transfer catalysts may be added.

The process according to the invention may be carried out in a wide temperature range of from about −80° C. to about 150° C., although it is preferably carried out at temperatures in the range of from −10° C. to about 100° C.

The process according to the invention may be carried out both continuously and also in batches. In batch operation, the base is preferably added to the 1-halogen phosphonosuccinic acid ester, although it is also possible simultaneously to introduce the base and the 1-halogen phosphonosuccinic acid ester into the reaction zone. The 1-halogen phosphonosuccinic acid ester may even be added to the base. The solvent(s) may be added both to the base and to the 1-halogen phosphonosuccinic acid ester or to both. However, it may also be independently added.

In general, the process according to the invention is carried out at normal pressure, although it may also be carried out under increased or reduced pressure. It can be advantageous to apply an increased pressure because of the resulting reduction in volatility, particularly of the bases and/or the solvents. Variations in pressure may also be utilized to shift the boiling point of the system into an optimal range, for example for vapor cooling.

The phosphonomaleic acid esters produced by the process according to the invention may be isolated by conventional methods. The base hydrohalides or the halides formed from the bases may be removed, for example, by filtration, centrifuging, etc., or by washing out with water or aqueous solutions. Alternatively, the phosphonomaleic acid ester itself may be extracted with a solvent, optionally after the previous addition of water. Solvent and unreacted bases may be completely or partly removed, for example by distillation, before or after separation of the base hydrohalide or the halide formed from the base. The phosphonomaleic acid ester produced in accordance with the invention may be further purified as a crude product and in solution by washing with water or with aqueous solutions of acids or bases or by contact with adsorbents and, after removal of the solvent, even by distillation.

The invention is illustrated by the following examples:

EXAMPLE 1

(a) Production of 1-chloro-1-dimethoxy phosphonosuccinic acid dimethyl ester:

530 ml of a bleaching liquor solution containing 86 g of active chlorine are added dropwise over a period of 5 minutes at 0° C. to 254 g of dimethoxy phosphonosuccinic acid dimethyl ester in 500 ml of water. During the reaction, some of the product precipitates as a second liquid phase from the initially homogeneous reaction solution. After the bleaching liquor has been added, 500 ml of methylene chloride are added for collecting the product, the organic phase is then separated off in a separation funnel and the aqueous phase is extracted three times with 200 ml of methylene chloride. Concentration in vacuo leaves 149 g of a residue of the combined organic phases. The 1-chloro-1-dimethoxy phosphonosuccinic acid dimethyl ester content of the residue amounts to 98.0%.

(b) Production of 1-bromo-1-dimethoxy phosphonosuccinic acid dimethyl ester:

A sodium hypobromite solution prepared from 190 g of bromine, 88 g of sodium hydroxide and 450 ml of water is added dropwise over a period of 1 hour at 0° C. to 254 g of dimethoxy phosphonosuccinic acid dimethyl ester in 1000 ml of methylene chloride. The reaction mixture is intensively stirred and externally cooled. After the hypobromite has been added, the reaction mixture is transferred to a separation funnel. The methylene chloride phase of higher specific gravity is removed and the residual aqueous solution is extracted once again with 300 ml of methylene chloride. The combined organic phases are concentrated, after which the residue is freed from volatile constituents in a water jet pump vacuum (14 Torr) at 100° C. According to analysis by gas chromatography, the residue, which weighs 302 g after this treatment, consists of 94.8% of 1-bromo-1-dimethoxy phosphonosuccinic acid dimethyl ester and 2.9% of dimethoxy phosphonosuccinic acid dimethyl ester. The 1-bromo-1-dimethoxy phosphonosuccinic acid dimethyl ester crystallizes on standing to form colorless needle-like crystals of high purity.

(c) Reaction of the product according to (a):

111 g of triethyl amine (1.1 mole) are added dropwise over a period of 1 hour at 20° to 25° C. to 288.5 g of 1-chloro-1-dimethoxy phosphonosuccinic acid dimethyl ester (1.0 mole) in 500 ml of toluene. After stirring for another 2 hours, the triethyl ammonium chloride precipitated is filtered off under suction and washed out with 250 ml of toluene. Toluene is distilled off from the solution under a vacuum of 14 Torr. The residue weighs 249 g. Subsequent distillation gives 123 g of distillate ($Bp_1$: 137° C.) and 100 g of a non-distillable sump product. According to analysis by gas chromatography, the distillate contains 98.2% of the required dimethoxy phosphonomaleic acid ester. $^1$H/NMR analysis shows that 88% of the product are present in the cis-form (phosphonomaleic acid form) and 12% in the transform (phosphonofumaric acid form).

Repeated distillation in vacuo gives a highly pure (>99%) product.

(d) Reaction of the product according to (b):

51 g of triethyl amine (0.5 mole) are added dropwise over a period of 30 minutes at 20° to 25° C. to 167 g of 1-bromo-1-dimethoxy phosphonosuccinic acid dimethyl ester (0.5 mole) in 300 ml of toluene. After stirring for another 50 minutes, the triethyl ammonium bromide precipitated is filtered off under suction and washed out with 200 ml of toluene. Toluene is distilled off from the solution under reduced pressure (up to 80° C./2 Torr). The residue weighs 122 g. Careful distillation by slowly introducing this residue dropwise into the heated flask of a vacuum distillation apparatus gives 84 g of dimethoxy phosphonomaleic acid dimethyl ester.

EXAMPLE 2

(a) 530 ml of a bleaching liquid solution containing 86 g (1.2 moles) of active chlorine are added dropwise over a period of 4 minutes at 0° C. to 254 g of dimethoxy phosphonosuccinic acid dimethyl ester (1.0 mole) in 1000 ml of methylene chloride. The reaction mixture is intensively stirred and externally cooled. After the bleaching liquor has been added, the reaction mixture is transferred to a separation funnel. The methylene chloride phase of higher specific gravity is removed and the residual aqueous solution is extracted once again with 100 ml of methylene chloride. The combined organic phases are concentrated, after which the residue is freed from volatile constituents in a water jet pump vacuum (14 Torr) at 100° C. According to analysis by gas chromatography, the residue, which weighs 268 g after this treatment, consists of 96.3% of 1-chloro-1-dimethoxy phosphonosuccinic acid dimethyl ester and 2.6% of dimethoxy phosphonosuccinic acid dimethyl ester.

(b) The procedure described in (a) is repeated with the difference that the reaction is carried out at 40° C. 234 g of crude 1-chloro-1-dimethoxy phosphonosuccinic acid dimethyl ester having a purity of 96.8%, as determined by gas chromatography, are obtained.

(c) The procedure described in (a) is repeated with the difference that only 500 ml of methylene chloride are used as solvent. 249 g of crude 1-chloro-1-dimethoxy phosphonosuccinic acid dimethyl ester having a purity of 97.3%, as determined by gas chromatography, are obtained.

(d) 125 g (1.0 mole) of DBN (2,3,4,6,7,8-hexahydropyrolo-[1,2-a]-pyrimidine) are added dropwise over a period of 1 hour at 15° to 20° C. to 288.5 g of 1-chloro-1-dimethoxy phosphonosuccinic acid dimethyl ester (1.0 mole) in 600 ml of toluene. After stirring for another 10 minutes, the salt precipitated is filtered off under suction and washed out with 300 ml of toluene. Toluene is distilled off from the solution under reduced pressure (up to 80° C./2 Torr). The residue weighs 258 g and its dimethoxy phosphonomaleic acid dimethyl ester content amounts to 94.6%.

EXAMPLE 3

152 g (1.0 mole) of DBU (2,3,4,6,7,8,9,10-octahydropyrimido[1,2-a]azepine) are added dropwise over a period of 1.5 hours at 20° to 25° C. to 288.5 g of 1-chloro-1-dimethoxy phosphonosuccinic acid dimethyl ester (1.0 mole) in 600 ml of toluene. After stirring for another 30 minutes, the salt precipitated is filtered off under suction and washed out with 300 ml of toluene. Toluene is distilled off from the solution under reduced pressure (up to 80° C./2 Torr). The residue weighs 261 g and, according to analysis by gas chromatography, consists of 96.2% pure dimethoxy phosphonomaleic acid dimethyl ester.

EXAMPLE 4

232 ml (1.0 mole) of 4.3 M methanolic sodium methylate are added dropwise over a period of 1 hour at 25° C. to 288.5 g of 1-chloro-1-dimethoxy phosphonosuccinic acid dimethyl ester (1.0 mole) in 250 ml of methanol. The sodium chloride precipitated is filtered off under suction and washed out with 150 ml of methanol. Methanol is distilled off from the solution under reduced pressure (up to 100° C./12 Torr). The residue weighs 293 g. 251 g of 99.8% pure dimethoxy phosphonomaleic acid dimethyl ester are obtained therefrom by distillation in vacuo.

EXAMPLE 5

2320 ml (1.0 mole) of 0.43 M methanolic sodium methylate are added dropwise over a period of 1 hour to 288.5 g of 1-chloro-1-dimethoxy phosphonosuccinic acid dimethyl ester (1.0 mole). The sodium chloride precipitated is filtered off under suction and washed out with 150 ml of methanol. Most of the methanol is distilled off. Sodium chloride subsequently precipitated is filtered off. The remaining methanol is distilled off in vacuo. Distillation in vacuo gives 221 g of dimethoxy phosphonomaleic acid dimethyl ester.

EXAMPLE 6

520 ml (1.0 mole) of 1.92 M ethanolic sodium ethylate are added dropwise over a period of 1 hour at 25° C. to 344.5 g (1.0 mole) of 1-chloro-1-diethoxy phosphonosuccinic acid diethyl ester (produced from diethoxy phosphonosuccinic acid diethyl ester and bleaching liquor in the same way as in Example 1(a) in 500 ml of ethanol. The sodium chloride precipitated is filtered off under suction and washed out with 150 ml of ethanol. Ethanol is distilled off from the solution under reduced pressure. Distillation of the residue in vacuo gives 259 g of diethoxy phosphonomaleic acid diethyl ester (Bp$_1$: 169° C).

EXAMPLE 7

152 g (1.0 mole) of DBU (2,3,4,6,7,8,9,10-octahydropyrimido[1,2-a]-azepine) are added dropwise over a period of 1 hour at 20° to 25° C. to 456.5 g (1.0 mole) of 1-chloro-1-di-i-butoxy phosphonosuccinic acid di-i-butyl ester (produced from di-i-butoxy phosphonosuccinic acid di-i-butyl ester and bleaching liquor in the same way as in Example 1(a) in 1000 ml of toluene. After stirring for another 60 minutes, the salt precipitated is filtered off under suction and washed out with 500 ml of toluene. Toluene is distilled off from the solution under reduced pressure (up to 120° C./2 Torr). The residue weighs 423 g and, according to analysis by gas chromatography, consists of 96.9% pure di-i-butoxy phosphonomaleic acid di-i-butyl ester.

EXAMPLE 8

64 g (0.6 mole) of sodium carbonate and 300 g of water are added dropwise to 268 g of a mixture of 1-methyl-1-(dimethoxy phosphono)-succinic acid dimethyl ester (40%) and 2-methyl-1-dimethoxy phosphonosuccinic acid dimethyl ester (60%, corresponding to 0.6 mole). 43 g (0.6 mole) of gaseous chlorine are introduced into this mixture over a period of 30 minutes at 20° C. The reaction mixture is intensively stirred and externally cooled. After the chlorine has been added, the reaction mixture is extracted three times with 200 ml of methylene chloride in a separation funnel. The combined organic phases are worked up in the same way as described in Example 1(a). According to analysis by gas chromatography, the residue, which weighs 205 g after this treatment, consists of 58% of 1-chloro-1-dimethoxy phosphono-2-methyl succinic acid dimethyl ester and 42% of the isomeric methyl dimethoxy phosphonosuccinic acid dimethyl ester.

104 g of this mixture, containing approximately 62 g (0.2 mole) of 1-chloro-1-dimethoxy phosphono-2-methyl succinic acid dimethyl ester, are initially introduced with 200 ml of methanol. 47 ml (0.2 mole) of 4.3 M methanolic sodium methylate are then added dropwise over a period of 30 minutes at 25° C. Sodium chloride precipitated is filtered off under suction and washed with a little methanol, and the solution is concentrated in vacuo. The residue is distilled. The distillate (Bp$_1$: 134°–148° C.) weighs 84 g and, according to $^1$H-NMR-analysis, consists of 54% of 1-dimethoxy phosphono-2-methyl maleic acid dimethyl ester and 46% of the isomeric methyl dimethoxy phosphonosuccinic acid dimethyl esters, among which the 1-methyl-1-phosphono isomer is predominant to a very large extent.

EXAMPLE 9

530 ml of a bleaching liquor solution containing 86 g (1.2 mole) of active chlorine are added dropwise over a period of 5 minutes at 0° C. to 238 g of methyl methoxy phosphonosuccinic acid dimethyl ester (1.0 mole) in 1000 ml of methylene chloride. The reaction mixture is intensively stirred and externally cooled. After the bleaching liquor has been added, the reaction mixture is transferred to a separation funnel. The methylene chloride phase of higher specific gravity is removed and the residual aqueous solution is extracted once again with 300 ml of methylene chloride. The combined organic phases are concentrated, after which the residue is freed from volatile constituents in a water jet pump vacuum (14 Torr) at 100° C. According to analysis by gas chromatography, the residue, which weighs 244 g after this treatment, consists of 82% of 1-chloro-1-(methyl methoxy phosphono)-succinic acid dimethyl ester and 13.2% of methyl methoxy phosphonosuccinic acid dimethyl ester.

133 g of this mixture, containing approximately 109 g (0.4 mole) of 1-chloro-1-(methyl methoxy phosphono)-succinic acid dimethyl ester, are initially introduced with 300 ml of methanol. 94 ml (0.4 mole) of 4.3 M methanolic sodium methylate are then added dropwise over a period of 10 minutes at 25° C. Sodium chloride precipitated is filtered off under suction, washed out with methanol and the filtrate is concentrated. Distillation gives 103 g of a product (Bp$_1$: 130°–135° C.), which, according to analysis by gas chromatography, consists of 88.5% of 1-(methyl methoxy phosphono)-maleic acid dimethyl ester and 10.6% of 1-(methyl methoxy phosphono)-succinic acid dimethyl ester.

EXAMPLE 10

530 ml of a bleaching liquor solution containing 86 g (1.2 mole) of active chlorine are added dropwise over a period of 5 minutes at 0° C. to 282 g (1.0 mole) of diethoxy phosphonosuccinic acid dimethyl ester (produced by the addition reaction between diethyl phosphite and maleic acid dimethyl ester) in 800 ml of methylene chloride. The reaction mixture is intensively stirred and externally cooled. After the bleaching liquor has been added, the reaction mixture is transferred to a separation funnel. The methylene chloride phase of higher specific gravity is removed and the residual aqueous solution is extracted twice with 300 ml of methylene chloride. The combined organic phases are concentrated, after which the residue is freed from volatile constituents in a water jet pump vacuum (14 Torr) at 100° C. According to analysis by gas chromatography, the residue, which weighs 285 g after this treatment, consists of 90.1% of dialkoxy 1-chloro-1-phosphonosuccinic acid ester and 2.8% of dialkoxy phosphonosuccinic acid ester. The gas chromatogram shows that a mixture of products formed through exchange of the methyl and ethyl ester groups is present instead of the expected, uniform 1-chloro-1-diethoxy phosphonosuccinic acid dimethyl ester. The $^1$H-NMR spectrum also indicates that, in addition to C$_2$H$_5$-O-P-groups, CH$_3$-O-P-groups are also present in substantially the same molar quantity.

175 g of this product, containing approximately 158 g of 1-chloro-1-phosphonosuccinic acid ester with two methoxy groups and two ethoxy groups on a statistical average as ester groups per molecule (corresponding to approximately 0.5 mole) are initially introduced with 200 ml of methanol. 140 ml of methanolic sodium methylate solution (0.6 mole) are then added dropwise over a period of 30 minutes at 20° C. The reaction mixture is then concentrated by distilling off the methanol in vacuo at no more than 20° C. After the addition of 100 ml of water, the solution is neutralized with sulphuric acid and subsequently extracted three times with 150 ml of methylene chloride. The combined organic extracts are concentrated and the residue is distilled. The distillate (Bp$_1$: 135°–145° C.) weighs 111 g. According to analysis by gas chromatography, it contains 78.7% of dimethoxy phosphonomaleic acid dimethyl ester and, in all, 19.8% of slightly higher boiling components. The $^1$H-NMR spectrum shows that the distillate contains methoxy groups and ethoxy groups in a ratio of 88:12. It follows from this that the higher boiling components are mixed methyl-ethyl esters of phosphonomaleic acid.

EXAMPLE 11

250 g of trimethyl phosphite (2.0 moles) are rapidly added at 100° C. to 288.5 g of 1-chloro-1-dimethoxy phosphonosuccinic acid dimethyl ester (1.0 mole). The resulting mixture is left boiling under reflux for 3 hours, during which time methyl chloride escapes and may be condensed by cooling. The volatile constituents are then distilled off in vacuo (up to 140° C./13 Torr). The volatile fraction consists essentially of dimethyl phosphite and trimethyl phosphite. The residue is distilled in vacuo (1 Torr). The distillate (Bp$_1$: 136°–138° C.) of dimethoxy phosphonomaleic acid dimethyl ester weighs 86 g.

EXAMPLE 12

4.6 g of sodium (0.2 mole) are finely dispersed in 200 ml of toluene by means of an Ultraturrax. 51 g of dimethoxy phosphonosuccinic acid dimethyl ester (0.2 mole) are slowly added dropwise to the suspension at 30° to 35° C. A clear, pale yellow solution of the sodium salt of dimethoxy phosphonosuccinic acid dimethyl ester is formed in an exothermic reaction.

The addition of this solution to a solution of 58 g of 1-chloro-1-dimethoxy phosphonosuccinic acid dimethyl ester in 200 ml of toluene kept at 25° to 30° C. results in the precipitation of sodium chloride. After the salt has been filtered off, the toluene is distilled off from the filtrate in vacuo. Distillation of the residue gives 88 g of a distillate which, according to analysis by $^1$H-NMR spectroscopy, is a substantially equimolar mixture of dimethoxy phosphonosuccinic acid dimethyl ester and dimethoxy phosphonomaleic acid dimethyl ester.

It will be appreciated that the instant specification and examples are set forth by way of illustration and not limitation, and that various modifications and changes may be made without departing from the spirit and scope of the present invention.

EXAMPLE 13

252 g of dimethoxy phosphono succinic acid dimethyl ester (1.0 mole) and 110 g of dimethyl phosphite are mixed. At a temperature between 20° and 25° C. 10 ml of a 4.3 molar solution of sodium methylate in methanol are added dropwise to that mixture. Already after addition of the first drops the exothermic reaction starts, such that the further addition has to be completed carefully. After completion of the reaction the mixture stands for additional 8 hours and then the mixture is heated to 120° C. at 2 Torr and the volatile parts are distilled off. The crystalline residue was 365 g.

According to gas chromatographic analysis the amount of 1.2-bis-dimethoxy phosphonosuccinic acid dimethylester was 95.5% of the volatile products. Recrystallization from toluene (twice) yields the 1.2-bis-dimethoxy phosphonosuccinic acid dimethyl ester of more than 99% purity (melting point 75° C.).

What is claimed is:

1. A process for producing a phosphonomaleic acid ester of the formula

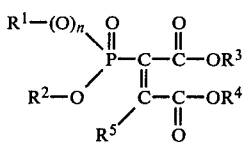

in which
R$^1$ is an optionally substituted alkyl radical containing from 1 to 16 carbon atoms and, where n=0, may also be an optionally substituted aryl radical,
R$^2$, R$^3$ and R$^4$ each independently is an optionally substituted alkyl radical containing from 1 to 16 carbon atoms,
R$^5$ is hydrogen, an alkyl or aryl radical containing from 1 to 7 carbon atoms, and
n=0 or 1,
comprising reacting a base with a 1-halogen-1-phosphonosuccinic acid ester of the formula

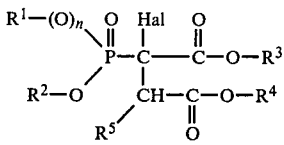

in which Hal is chlorine or bromine.

2. A process according to claim 1 in which
R$^1$ is alkyl or alkoxyalkyl containing from 1 to 12 carbon atoms in each alkyl moiety and, where n=0, may also be phenyl,
R$^2$, R$^3$ and R$^4$ each independently is alkyl or alkoxyalkyl containing from 1 to 12 carbon atoms in each alkyl moiety, and
R$^5$ is hydrogen or methyl.

3. A process according to claim 2, in which
R$^1$ is alkyl or alkoxyalkyl containing from 1 to 4 carbon atoms in each alkyl moiety and, where n=0, may also be phenyl, and
R$^2$, R$^3$ and R$^4$ each independently is alkyl or alkoxyalkyl containing from 1 to 4 carbon atoms in each alkyl moiety.

4. A process according to claim 3, in which
R$^1$ is methyl, ethyl, methoxymethyl, methoxyethyl, ethoxymethyl, ethoxyethyl or phenyl, and
R$^2$, R$^3$ and R$^4$ each independently is methyl, ethyl, methoxymethyl, methoxyethyl, ethoxymethyl or ethoxyethyl.

* * * * *